(12) United States Patent
Bae et al.

(10) Patent No.: US 10,827,987 B2
(45) Date of Patent: Nov. 10, 2020

(54) X-RAY IMAGE PROCESSING DEVICE AND METHOD FOR RECONSTRUCTING PROJECTION IMAGE OBTAINED USING SMALL X-RAY DETECTOR

(71) Applicants: VATECH Co., Ltd., Gyeonggi-do (KR); VATECH EWOO Holdings Co., Ltd., Gyeonggi-do (KR)

(72) Inventors: Woong Bae, Gyeonggi-do (KR); Sang Og Na, Gyeonggi-do (KR); Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 58 days.

(21) Appl. No.: 16/088,166

(22) PCT Filed: Mar. 27, 2017

(86) PCT No.: PCT/KR2017/003283
§ 371 (c)(1),
(2) Date: Sep. 25, 2018

(87) PCT Pub. No.: WO2017/164720
PCT Pub. Date: Sep. 28, 2017

(65) Prior Publication Data
US 2019/0216410 A1    Jul. 18, 2019

(30) Foreign Application Priority Data
Mar. 25, 2016 (KR) .......... 10-2016-0036146

(51) Int. Cl.
*A61B 6/03* (2006.01)
*G06T 5/50* (2006.01)
(Continued)

(52) U.S. Cl.
CPC ............ *A61B 6/032* (2013.01); *A61B 6/00* (2013.01); *A61B 6/03* (2013.01); *A61B 6/4452* (2013.01);
(Continued)

(58) Field of Classification Search
None
See application file for complete search history.

(56) References Cited

U.S. PATENT DOCUMENTS

2005/0213705 A1  9/2005  Hoffman
2012/0059239 A1  3/2012  Yamaguchi
(Continued)

FOREIGN PATENT DOCUMENTS

EP   3175787 A1      6/2017
JP   2003-180672 A   7/2003
(Continued)

OTHER PUBLICATIONS

European Patent Office, European Search Report of corresponding EP Patent Application No. 17770690.0, dated Oct. 18, 2019.
(Continued)

*Primary Examiner* — Hoon K Song
(74) *Attorney, Agent, or Firm* — IP Legal Services, LLC

(57) ABSTRACT

The present invention relates to an X-ray image processing device and an X-ray image processing method using a small X-ray detector, in which the device includes a controller configured to control an X-ray source and an X-ray detector to obtain m (m is an integer of 2 or more) number of consecutive divided projection images at each of preset n (n is an integer of 1 or more) number of imaging angles while rotating around a rotary axis and facing each other, a projection image synthesizing unit configured to generate a synthetic projection image by synthesizing the m number of divided projection images obtained in correspondence to each imaging angle, and an image reconstructor configured to generate a reconstructed image by reconstructing the synthetic projection image.

8 Claims, 15 Drawing Sheets

(51) Int. Cl.
    *G06T 11/60*     (2006.01)
    *A61B 6/00*     (2006.01)
    *G06T 11/00*     (2006.01)

(52) U.S. Cl.
    CPC .......... *A61B 6/5229* (2013.01); *A61B 6/5258* (2013.01); *G06T 5/50* (2013.01); *G06T 11/008* (2013.01); *G06T 11/60* (2013.01); *G06T 2210/41* (2013.01)

(56) References Cited

U.S. PATENT DOCUMENTS

| | | |
|---|---|---|
| 2013/0077749 A1 | 3/2013 | Akahori et al. |
| 2013/0223585 A1* | 8/2013 | Tsukagoshi .......... G01N 23/046 378/4 |
| 2014/0064450 A1 | 3/2014 | Yamaguchi |
| 2014/0140481 A1 | 5/2014 | Yamaguchi |
| 2016/0213336 A1 | 7/2016 | Kim et al. |
| 2017/0245812 A1 | 8/2017 | Choi |

FOREIGN PATENT DOCUMENTS

| | | |
|---|---|---|
| JP | 2012-055475 A | 3/2012 |
| JP | 2013-198724 A | 10/2013 |
| KR | 10-2015-0024736 A | 3/2015 |
| KR | 10-2016-0014537 A | 2/2016 |
| WO | 2016/018002 A1 | 2/2016 |

OTHER PUBLICATIONS

European Patent Office, European Search Report of corresponding EP Patent Application No. 17770690.0, dated Sep. 11, 2020.

* cited by examiner

X-RAY IMAGE PROCESSING DEVICE AND METHOD FOR RECONSTRUCTING PROJECTION IMAGE OBTAINED USING SMALL X-RAY DETECTOR

CROSS REFERENCE TO RELATED APPLICATIONS

This application is a National Stage Patent Application of PCT International Patent Application No. PCT/KR2017/003283 (filed on Mar. 27, 2017) under 35 U.S.C. § 371, which claims priority to Korean Patent Application No. 10-2016-0036146 (filed on Mar. 25, 2016), the teaching of which are incorporated herein in their entireties by reference.

TECHNICAL FIELD

The present invention relates generally to an X-ray image processing device and a method for reconstructing a field of view (FOV) using a projection image. More particularly, the present invention relates to an X-ray image processing device and a method for reconstructing a three-dimensional image of the entire FOV using small projection images having a width smaller than half of the width of a field of view (FOV) obtained by a small X-ray detector.

BACKGROUND ART

In general, an X-ray image processing device includes an X-ray source and an X-ray detector, and a CT image requires an expensive large X-ray detector.

Accordingly, to reduce the manufacturing cost of an X-ray image processing device for manufacturers and to reduce the maintenance cost of an X-ray image processing device for users, an X-ray image processing device that uses a small X-ray detector is required, and as a result, manufacturers produce an X-ray image processing device that reconstructs an FOV with a small detector, for example, with a half-beam detector in which the length thereof in the width direction intersecting a rotating axis is equal to or more than ½ of the width of the FOV.

However, since the width of the half-beam detector is still large, it is difficult to significantly reduce the manufacturing cost of the X-ray image processing device. Further, when the width of the X-ray detector is reduced, the FOV of the X-ray image processing device is correspondingly reduced, which increases the possibility that a field of interest of a subject is not sufficiently secured. Therefore, it is not easy to reduce the width of the X-ray detector more than the half-beam detector.

DISCLOSURE

Technical Problem

Accordingly, the present invention intends to provide an X-ray image processing device configured to obtain a multi-directional projection image using a small X-ray detector having a width smaller than the width of a conventional X-ray detector, specifically having a width less than 50% of the width of the FOV, and to reconstruct a three-dimensional image of the entire FOV using the obtained projection image.

Further, the present invention intends to provide a three-dimensional image of a large FOV having a width greater than 50% of the width of the X-ray detector, while a small X-ray detector is used.

Technical Solution

In order to achieve the above object, according to some aspects of the present invention, there is provided an X-ray image processing method including: (a) obtaining m (m is an integer of 2 or more) number of divided projection images at each of predetermined n (n is an integer of 1 or more) number of imaging angles about a rotating axis by moving an X-ray detector in a width direction across the rotating axis while rotating an X-ray source and the X-ray detector with the same facing each other about the rotating axis interposed therebetween; (b) generating a synthetic projection image at each of the imaging angles using the m number of divided projection images at each of the imaging angles; and (c) generating a reconstructed image by reconstructing the synthetic projection image.

Here, in the (a) step, the X-ray source and the X-ray detector may be rotated m*360 degrees.

After the (a) step and before the (c) step, the method may further include correcting the m number of divided projection images at each of the imaging angles with a same imaging angle for the rotating axis.

In particular, after the (a) step and before the (c) step, multiple reference projection images at each imaging angle may be obtained from the predetermined n number of imaging angles and multiple imaging angles adjacent thereto; a projection image closest to the m number of projection images at each of the imaging angles may be obtained; and imaging angles of the m number of projection images at each of the imaging angles may be corrected along an imaging angle of the closest projection image at each of the imaging angles, whereby the m number of divided projection images at each of the imaging angles are corrected with the same imaging angle for the rotating axis.

Meanwhile, according to some aspects of the present invention, there is provided an X-ray image processing device including: a divided projection image obtaining unit configured to obtain m (m is an integer of 2 or more) number of divided projection images at each of predetermined n (n is an integer of 1 or more) number of imaging angles about a rotating axis by moving an X-ray detector in a width direction across the rotating axis while rotating an X-ray source and the X-ray detector with the same facing each other about the rotating axis interposed therebetween; a projection image synthesizing unit configured to generate a synthetic projection image at each of the imaging angles using the m number of divided projection images at each of the imaging angles; and an image reconstructor configured to generate a reconstructed image by reconstructing the synthetic projection image.

Here, the divided projection image obtaining unit may rotate the X-ray source and the X-ray detector m*360 degrees.

Further, the image reconstructor may correct the m number of divided projection images at each of the imaging angles with a same imaging angle for the rotating axis to generate the reconstructed image.

In particular, the image reconstructor may obtain multiple reference projection images at each imaging angle from the predetermined n number of imaging angles and multiple imaging angles adjacent thereto, obtain a projection image closest to the m number of projection images at each of the imaging angles, and correct imaging angles of the m number of projection images at each of the imaging angles along an imaging angle of the closest projection image at each of the imaging angles, thereby correcting the m number of divided projection images at each of the imaging angles with the same imaging angle for the rotating axis.

Advantageous Effects

The present invention provides an X-ray image processing device configured to obtain a multi-directional projection image using a small X-ray detector having a width smaller than the width of a conventional X-ray detector, specifically having a width less than 50% of the width of an FOV, and to reconstruct a three-dimensional image of the entire FOV using the obtained projection image.

Since the present invention uses a small X-ray detector having a width smaller than the width of a conventional X-ray detector, specifically having a width less than 50% of the width of an FOV, manufacturing cost is reduced.

Further, the present invention provides a three-dimensional image of a large FOV having a width greater than 50% of the width of the X-ray detector, while a small X-ray detector is used.

MODE FOR INVENTION

Detailed features and advantages of the present invention will be apparent from the following detailed description based on the accompanying drawings. However, it should be understood that the embodiment of the present invention may be changed to a variety of embodiments and the scope and spirit of the present invention are not limited to the embodiment described hereinbelow. The embodiment of the present invention described hereinbelow is provided for allowing those skilled in the art to more clearly comprehend the present invention.

It will be understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof. It will be further understood that the singular forms "a," "an" and "the" are intended to include the plural forms as well, unless the context clearly indicates otherwise.

Figure 1:
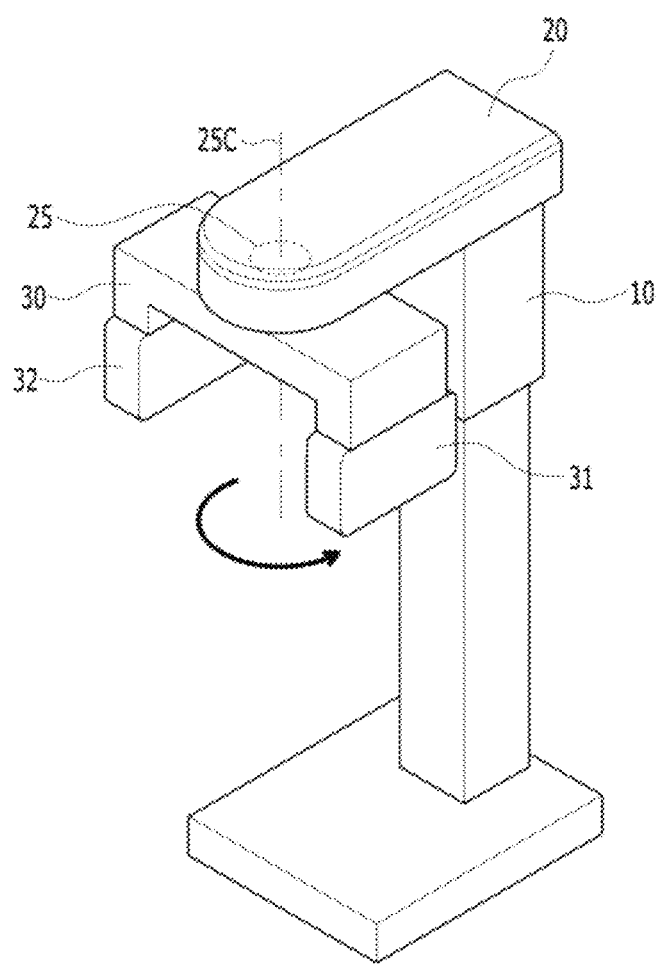
FIG. 1 is a view showing an X-ray image processing device according to an embodiment of the present invention.

FIG. 1 is a view showing an X-ray image processing device according to an embodiment of the present invention for reconstructing a projection image obtained using a small X-ray detector (hereinafter, referred to as an "X-ray image processing device").

As shown in FIG. 1, an X-ray image processing device according to the embodiment of the present invention includes: a main body 10, a support 20 connected to a side of the main body 10, a rotating arm 30 connected to a side of the support 20, an X-ray detector unit 31 disposed on a first side of the rotating arm 30 about a rotating axis 25C, and an X-ray generator 32 disposed on a second side of the rotating arm 30 opposite to the X-ray detector unit 31 about the rotating axis 25C. The X-ray image processing device according to the embodiment of the present invention includes a rotation drive device 25 provided between the rotating arm and the support 20, and is configured to rotate the rotating arm 30 about the rotating axis 25C, whereby the X-ray detector unit 31 and the X-ray generator 32 rotate about the rotating axis 25C.

FIGS. 2*a* to 2*d* are views showing the X-ray detector unit 31, the X-ray generator 32, and a controller 70 of the X-ray image processing device according to the embodiment of the present invention.

As shown in FIGS. 2*a* to 2*d*, when dividing a field of view (FOV) into multiple concentric circles of the same radius, the X-ray detector unit 31 includes: an X-ray detector 311 configured to receive X-rays with a width corresponding to each FOV FA, FB, FC, FD of the concentric circles; and an X-ray detector driver 312 configured to move the X-ray detector 311 in the tangential direction of the rotating direction of the rotating axis 25C (i.e., the width direction of the X-ray detector 311), wherein the X-ray detector driver 312 may include a motor 315 generating power, a drive shaft 314 transmitting the power, and a connector 313 connecting the X-ray detector 311 and the drive shaft 314 together. For reference, in this specification, the longitudinal direction of the X-ray detector 311 refers to a direction parallel to the rotating axis 25C, and the width direction of the X-ray detector 311 refers to a direction crossing the rotating axis 25C, for example, a direction perpendicular to the rotating axis 25C.

As shown in FIGS. 2*a* to 2*d*, the X-ray generator 32 includes: an X-ray source 321 capable of irradiating X-rays; and a collimator 322 adjusting the width and direction of the X-rays irradiated by the X-ray source 321 according to the width and position of the X-ray detector 311, wherein collimator 322 may include a collimator window or collimator blade 323 made of a material that absorbs X-rays, for example, a material such as lead (Pb). Further, the collimator 322 may include a motor 324 generating power capable of moving at least one collimator window or collimator blade 323, a drive shaft 325 transmitting the power, and a connector 326 connecting a part of the collimator window or collimator blade 323 and the drive shaft 325 together.

As shown in FIGS. 2*a* to 2*d*, the controller 70 controls the rotation drive device 25 to rotate the rotating arm 30, thereby rotating the X-ray detector unit 31 and the X-ray generator 32 disposed at opposite sides thereof while facing each other. On the other hand, the controller is connected with both the X-ray detector unit 31 and the X-ray generator 32 to control the motor 315 of the X-ray detector unit 31 and the motor 324 of the X-ray generator 32, thereby controlling the drive of the X-ray detector 311 and the X-ray source 321, respectively.

Therefore, to sum up the above description, it is understood that the controller 70 can control the X-ray source 321 to irradiate X-rays as wide as the X-ray detector 311 to the place where the X-ray detector 311 is located.

As shown in FIGS. 2a to 2d, the concentric circles centering on the rotating axis 25C represent FOVs FA, FB, FC, and FD corresponding to the consecutive light receiving positions 311A, 311B, 311C, and 311D of the X-ray detector 311, respectively.

The X-ray image processing device is provided with a divided projection image obtaining unit configured to obtain a multi-directional divided projection image through the movement of the X-ray detector 311 in the width direction and the rotation of the X-ray detector 311 and the X-ray source 321 about the rotating axis 25C while facing each other.

A method of obtaining the multi-directional divided projection image will be described with reference to FIGS. 2a and 2d.

The multi-directional divided projection image is obtained as follows. Firstly, the X-ray detector 311 is disposed at an initial light-receiving position among m number of light-receiving positions that correspond to each FOV of the entire FOV constituted by m (m is a natural number of 2 or more) number of concentric FOVs and are continuous with each other, and the X-ray detector 311 and the X-ray source 321 are aligned along a reference axis 25D passing the rotating axis 25C by rotating the rotating arm 30. Next, the rotating arm 30 is rotated to rotate the X-ray detector 311 and the X-ray source 321 at angles of 360 degrees about the rotating axis 25C while facing each other. While the rotating arm 30 is rotated 360 degrees, the X-ray source 321 irradiates the X-rays to the X-ray detector 311 at each of n (n is a natural number of 1 or more) number of predetermined imaging angles θ based on the rotating axis 25C, whereby the X-ray detector 311 obtains n number of multi-directional divided projection images.

Next, the X-ray detector 311 is moved in the width direction thereof by the width ω of the X-ray detector 311 and placed at a light receiving position corresponding to a next FOV. Next, the rotating arm 30 is rotated to rotate the X-ray detector 311 and the X-ray source 321 at angles of 360 degrees about the rotating axis 25C while facing each other. While the rotating arm 30 is rotated 360 degrees, the X-ray source 321 irradiates the X-rays to the X-ray detector 311 at each of n (n is a natural number of 1 or more) number of predetermined imaging angles θ based on the rotating axis 25C, whereby the X-ray detector 311 obtains n number of multi-directional divided projection images.

In the same manner as described above, the X-ray detector 311 is moved in the width direction of the X-ray detector 311 to be arranged at m number of light receiving positions, and relatively rotated 360 degrees to obtain a total of m×n number of divided projected images.

Referring to the foregoing description and FIGS. 2a and 2d, for example, a method of acquiring a divided projection image in which m is set to 4 and n is set to 8 is as follows.

Figure 2A:
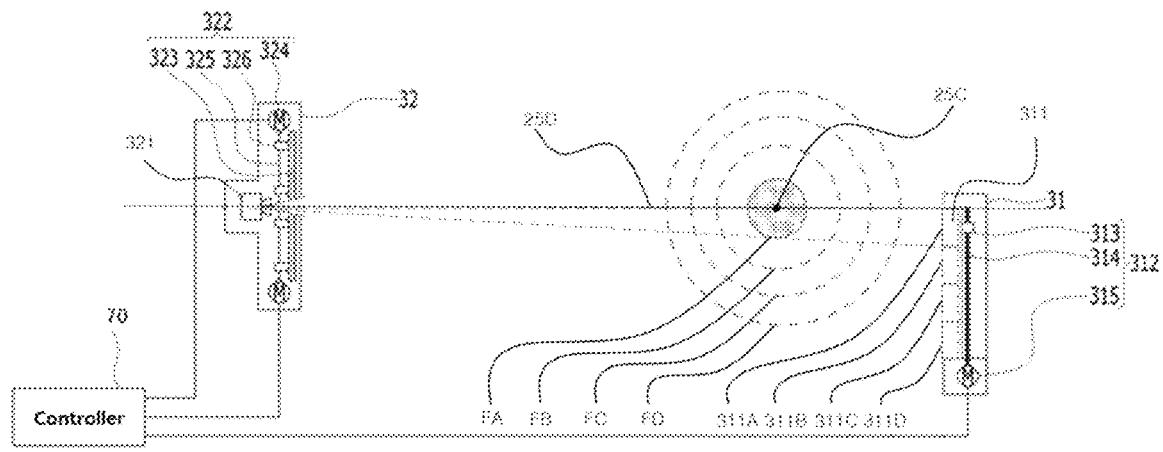
FIGS. 2*a* to 2*d* are views showing an X-ray detector unit, an X-ray generator, and a controller of the X-ray image processing device according to the embodiment of the present invention.

Firstly, as shown in FIG. 2a, X-ray detector 311 is moved to a first light receiving position 311A indicated by the solid line. Next, the rotating arm 30 rotates the X-ray detector 311 and the X-ray source 321 at angles of 360 degrees about the rotating axis 25C with the same facing each other. While the rotating arm 30 is rotated 360 degrees, the X-ray source 321 irradiates the X-rays to the X-ray detector 311 at each of eight predetermined imaging angles θ based on the rotating axis 25C, whereby the X-ray detector 311 obtains eight multi-directional divided projection images corresponding to a first FOV FA.

Figure 2B:
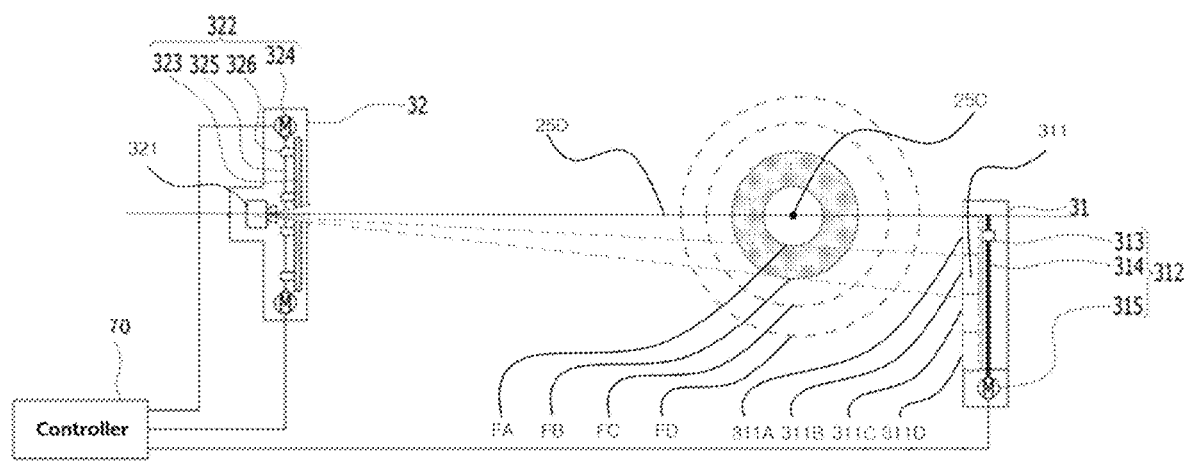

Next, as shown in FIG. 2b, the X-ray detector 311 is moved from the first light receiving position 311A to a second light receiving position 311B in the width direction thereof by the width ω of the X-ray detector 311. Next, the rotating arm 30 rotates the X-ray detector 311 and the X-ray source 321 at angles of 360 degrees about the rotating axis 25C while facing each other. While the rotating arm 30 is rotated 360 degrees, the X-ray source 321 irradiates the X-rays to the X-ray detector 311 at each of eight predetermined imaging angles θ based on the rotating axis 25C, whereby the X-ray detector 311 obtains eight multi-directional divided projection images corresponding to a second FOV FB.

Figure 2C:
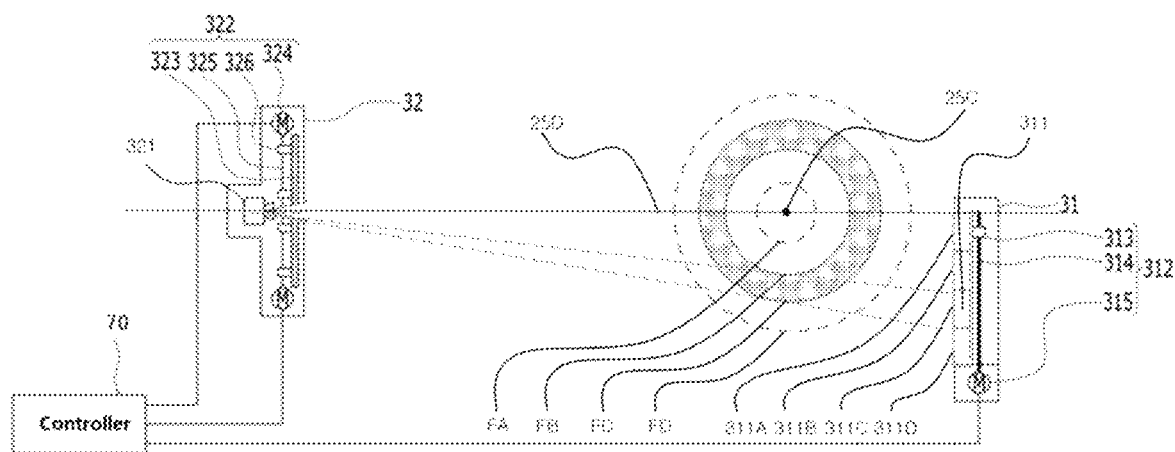

Next, as shown in FIG. 2c, the X-ray detector 311 is moved from the second light receiving position 311B to a third light receiving position 311C in the width direction thereof by the width ω of the X-ray detector 311. Next, the rotating arm 30 rotates the X-ray detector 311 and the X-ray source 321 at angles of 360 degrees about the rotating axis 25C while facing each other. While the rotating arm 30 is rotated 360 degrees, the X-ray source 321 irradiates the X-rays to the X-ray detector 311 at each of eight predetermined imaging angles θ based on the rotating axis 25C, whereby the X-ray detector 311 obtains eight multi-directional divided projection images corresponding to a third FOV FC.

Figure 2D:
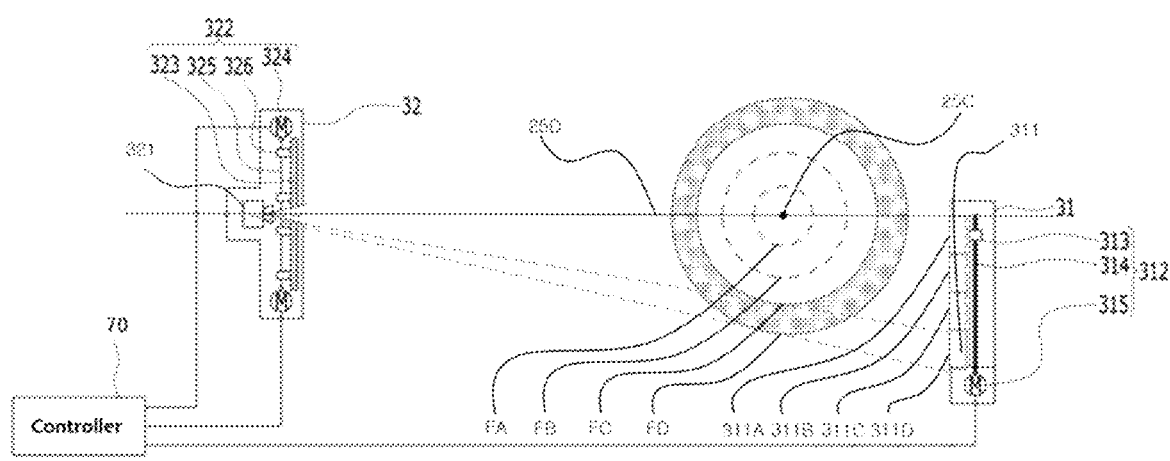

Next, as shown in FIG. 2d, the X-ray detector 311 is moved from the third light receiving position 311C to a fourth light receiving position 311D in the width direction thereof by the width ω of the X-ray detector 311. Next, the rotating arm 30 rotates the X-ray detector 311 and the X-ray source 321 at angles of 360 degrees about the rotating axis 25C while facing each other. While the rotating arm 30 is rotated 360 degrees, the X-ray source 321 irradiates the X-rays to the X-ray detector 311 at each of eight predetermined imaging angles θ based on the rotating axis 25C, whereby the X-ray detector 311 obtains eight multi-directional divided projection images corresponding to a fourth FOV FD.

As seen from FIGS. 2a to 2d, an exemplarily divided projection image corresponds to a quarter of the size of a projection image (hereinafter, referred to as a "half-beam image") in which a subject is imaged with a half beam. However, it should be understood that the relative size of the projected image to the half-beam image is not limited thereto, and may vary depending on the number of times that the X-ray detector 311 is moved in the width direction of the X-ray detector 311. For example, unlike the example presented in FIGS. 2a to 2d, when the X-ray detector 311 is moved one time in the direction of the drive shaft 314 instead of three times to acquire a multi-directional divided projection image at two light receiving positions, the size of the divided projection image will correspond to half the size of the half-beam image. Of course, in such a case, the size of the entire FOV would be reduced by half in comparison with the example presented in FIGS. 2a to 2d.

Meanwhile, the predetermined imaging angles e is angles where the X-ray detector 311 and the X-ray source 321 are rotated while facing each other to obtain multi-directional divided projections images required to reconstruct the entire FOV FA, FB, FC, and FD into a three-dimensional image.

For example, when multi-directional divided projections images required for reconstruction in a three-dimensional image are obtained by rotating every 45 degrees with respect to the rotating axis 25C, the predetermined imaging angle may be 0, 45, 90, 135, 180, 225, 270, and 315 degrees based on the rotating axis 25C.

For example, when the X-ray source 321 is rotated by 45 degrees with respect to the rotating axis 25C at each of the light receiving positions 311A, 311B, 311C, and 311D and obtains multi-directional divided projection images, a total of 32 divided projections images A1 to A8, B1 to B8, C1 to C8, and D1 to D8 are obtained, which are shown in Table 1 below.

TABLE 1

| Light receiving position | Imaging angle (θ) | | | | | | |
|---|---|---|---|---|---|---|---|
| | 0° | 45° | 90° | 135° | 180° | 225° | 270° | 315° |
| 311A | A1 | A2 | A3 | A4 | A5 | A6 | A7 | A8 |
| 311B | B1 | B2 | B3 | B4 | B5 | B6 | B7 | B8 |
| 311C | C1 | C2 | C3 | C4 | C5 | C6 | C7 | C8 |
| 311D | D1 | D2 | D3 | D4 | D5 | D6 | D7 | D8 |

As seen from Table 1, the obtained multi-directional divided projected images are stored in an internal storage unit (not shown) according to the command of the controller 70 together with the imaging angle information and the light receiving position information upon acquisition for each multi-directional divided projected image. For example, in the case of a divided projection image C2, the imaging angle information is 45 degrees and the light receiving position information is the third light receiving position 311C.

FIGS. 3a to 3d are views exemplarily showing projection images obtained according to the embodiment of the present invention.

Figure 3A:
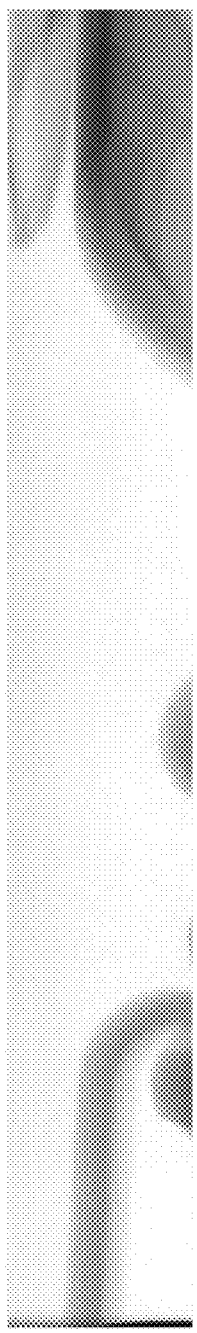
FIGS. 3*a* to 3*d* are views exemplarily showing projection images obtained according to the embodiment of the present invention.
Figure 3B:
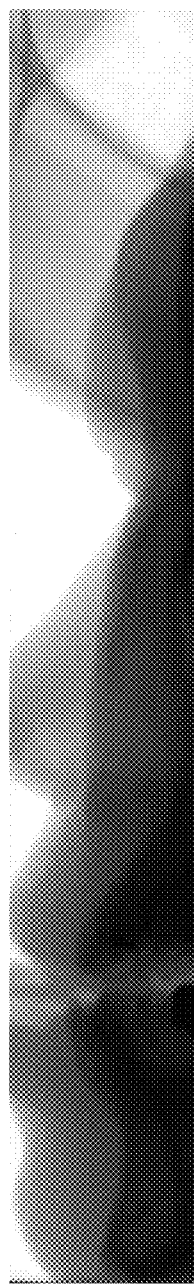
Figure 3C:
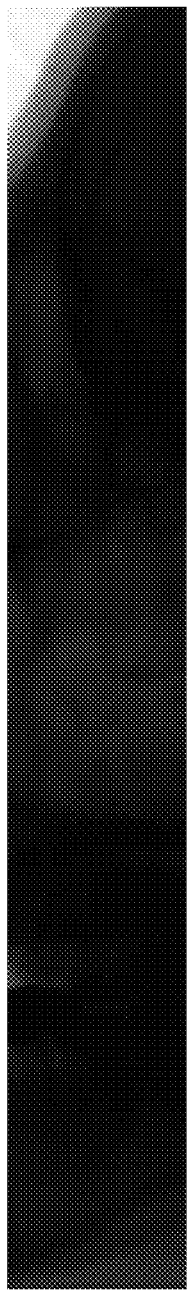
Figure 3D:
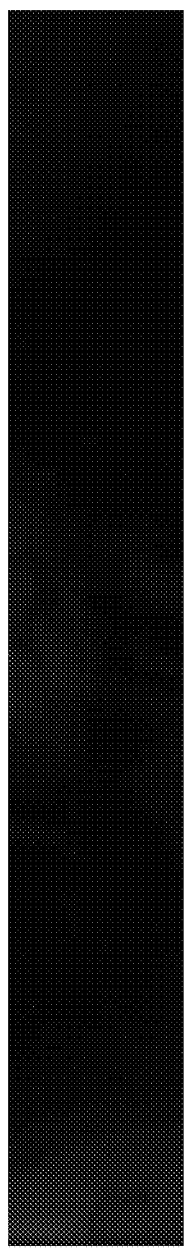

FIG. 3a is a view exemplarily showing a divided projection image (that is, corresponding to A2 in Table 1) in which the imaging angle information is 45 degrees and the light receiving position information is the first light receiving position 311A, FIG. 3b is a view exemplarily showing a divided projection image (that is, corresponding to B2 in Table 1) in which the imaging angle information is 45 degrees and the light receiving position information is the second light receiving position 311B, FIG. 3c is a view exemplarily showing a divided projection image (that is, corresponding to C2 in Table 1) in which the imaging angle information is 45 degrees and the light receiving position information is the third light receiving position 311C, and FIG. 3d is a view exemplarily showing a divided projection image (that is, corresponding to D2 in Table 1) in which the imaging angle information is 45 degrees and the light receiving position information is the fourth light receiving position 311D.

Figure 4:
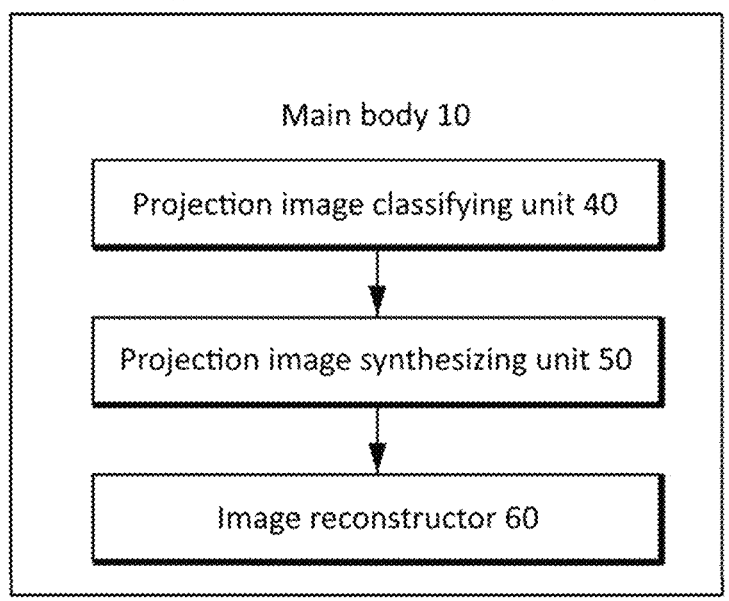
FIG. 4 is a view showing a main body of the X-ray image processing device according to the embodiment of the present invention.

As shown in FIG. 4, the main body 10 includes a projection image classifying unit 40, a projection image synthesizing unit 50, and an image reconstructor 60.

The projection image classifying unit 40 classifies each divided projection image stored in the storage unit into an associated image group according to the imaging angle information.

Taking the multi-directional divided projection images shown in Table 1 as an example, a divided projection image A1 having the imaging angle information of 0 degree among the divided projection images A1 to A8 in which the light receiving position information is the first light receiving position 311A, a divided projection image B1 having the imaging angle information of 0 degree among the divided projection images B1 to B8 in which the light receiving position information is the second light receiving position 311B, a divided projection image C1 having the imaging angle information of 0 degree among the divided projection images C1 to C8 in which the light receiving position information is the third light receiving position 311C, and a divided projection image D1 having the imaging angle information of 0 degree among the divided projection images D1 to D8 in which the light receiving position information is the fourth light receiving position 311D are classified as a first associated image group. Likewise, divided projection images A2, B2, C2, and D2 having the imaging angle information of 45 degrees are classified as a second associated image group, divided projection images A3, B3, C3, and D3 having the imaging angle information of 90 degrees are classified as a third associated image group, divided projection images A4, B4, C4, and D4 having the imaging angle information of 135 degrees are classified as a fourth associated image group, divided projection images A5, B5, C5, and D5 having the imaging angle information of 180 degrees are classified as a fifth associated image group, divided projection images A6, B6, C6, and D6 having the imaging angle information of 225 degrees are classified as a sixth associated image group, divided projection images A7, B7, C7, and D7 having the imaging angle information of 270 degrees are classified as a seventh associated image group, and divided projection images A8, B8, C8, and D8 having the imaging angle information of 315 degrees are classified as an eighth associated image group. In this way, projection images for each column of Table 1 are classified as associated image groups. In this manner, the projection image classifying unit 40 classifies the divided projection images according to the imaging angle information.

Next, the projection image synthesizing unit 50 generates n number of synthetic projection images based on the light receiving position information for m number of divided projection images in n number of associated image groups. The synthesis of m divided projections images in one associated image group into one synthetic projection image is intended to eliminate the discontinuity due to the difference in contrast between the divided projection images.

For example, the first associated image group A1, B1, C1, and D1 can be synthesized in the order of the first, second, third and fourth light receiving positions 311A, 311B, 311C and 311D according to the light receiving position information or in the reverse order to obtain one synthetic projection image.

When synthesizing the divided projection images in one associated image group, a multi-band blending algorithm generally used for synthesizing images can be used. The multi-band blending algorithm is known from "A Multiresolution Spline With Application to Image Mosaics," by Burt and Adelson in ACM Transactions on Graphics, October 1983. When using the multi-band blending algorithm, the high-frequency region of the overlapped portion of the divided projection images is relatively narrowly and the low-frequency region is relatively broadly synthesized, thereby effectively synthesizing the detail components of the projection image. The present invention is not limited to the multi-band blending algorithm, and a similar synthesis algorithm may be applied to the present invention.

Meanwhile, the synthetic projection image generated using the divided projection images in a specific associated image group has the imaging angle information and the light receiving position information of the corresponding divided projection image.

Figure 5:
FIG. 5 is a view showing a synthetic projection image where the projection images of FIGS. 3*a* to 3*d* are synthesized.

FIG. 5 is a view showing an image where the projection images of FIGS. 3a to 3d are synthesized into one synthetic projection image.

The image reconstructor 60 reconstructs n number of synthetic projection images to obtain a three-dimensional reconstructed image. Synthetic projection images can be reconstructed into a three-dimensional image using a Filtered Back Projection algorithm such as FDK (Feldkamp, Davis and Kress) algorithm or iterative reconstruction algorithm used for three-dimensional image reconstruction.

For example, referring to FIGS. 6a to 6e, reference will be made to a process where using the iterative reconstruction algorithm, the image reconstructor 60 reconstructs synthetic projection images to obtain a three-dimensional reconstructed image.

Firstly, the synthetic projection image is constituted by divided projection images, and each of the divided projection images is constituted by multiple pixels, wherein the back projection of one predetermined pixel in each divided projection image of the synthetic projection image is exemplarily described herein.

Figure 6A:
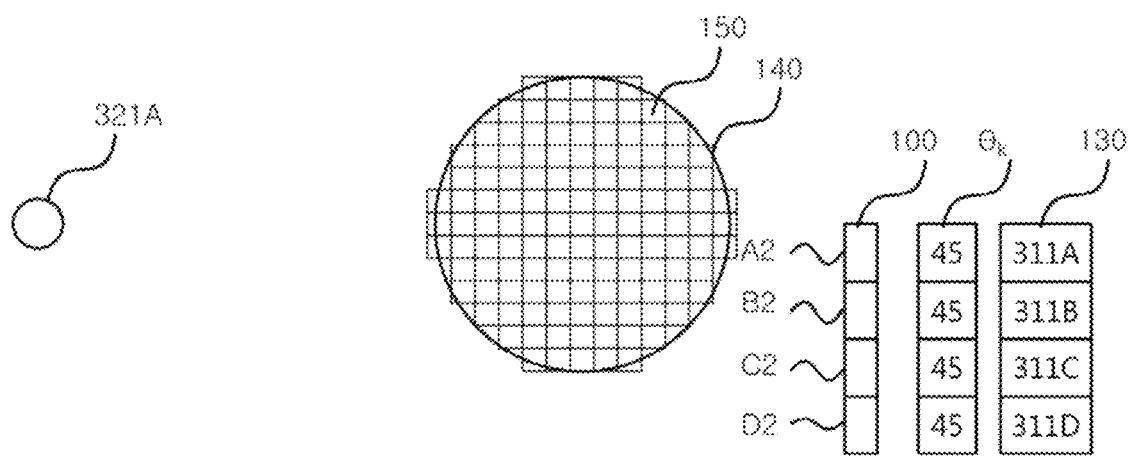
FIGS. 6*a* to 6*e* are views showing processes of reconstructing the synthetic projection image.
Figure 6B:
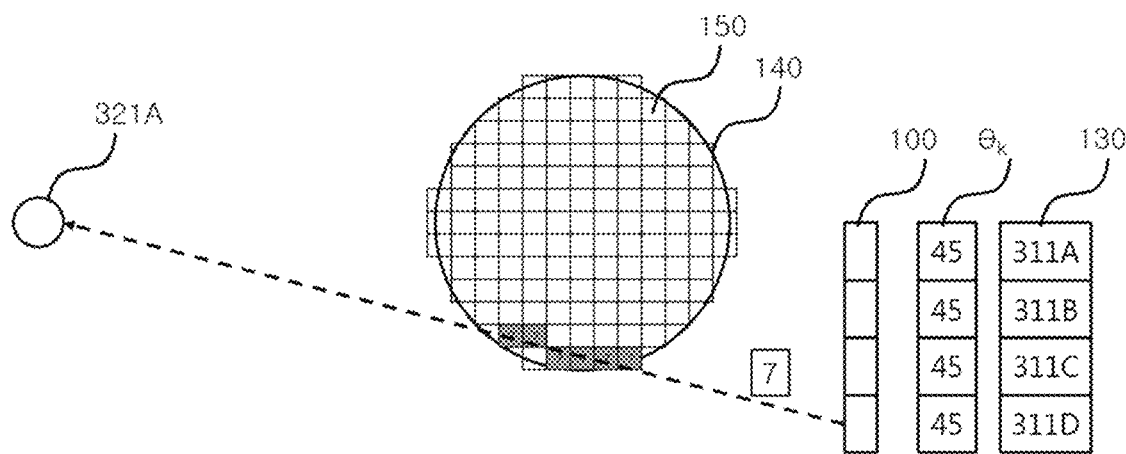
Figure 6C:
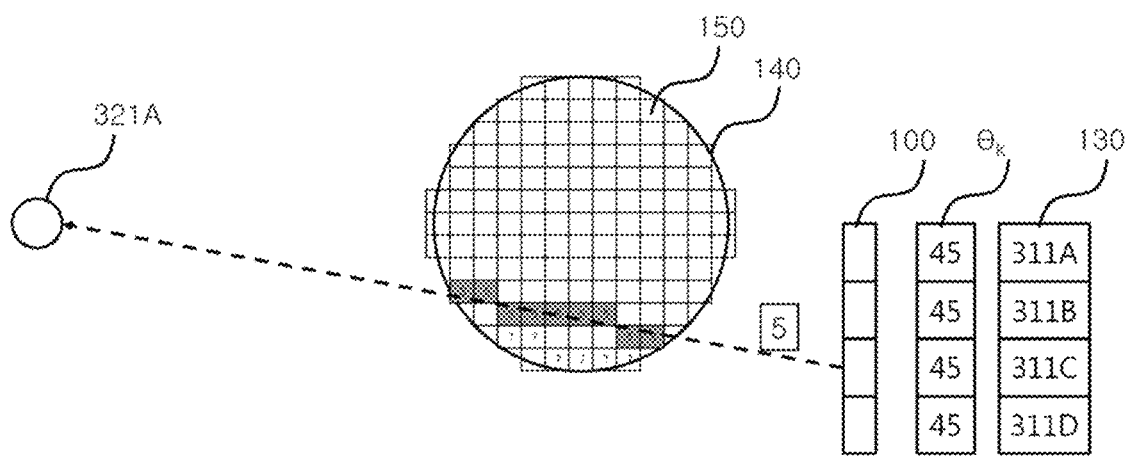
Figure 6D:
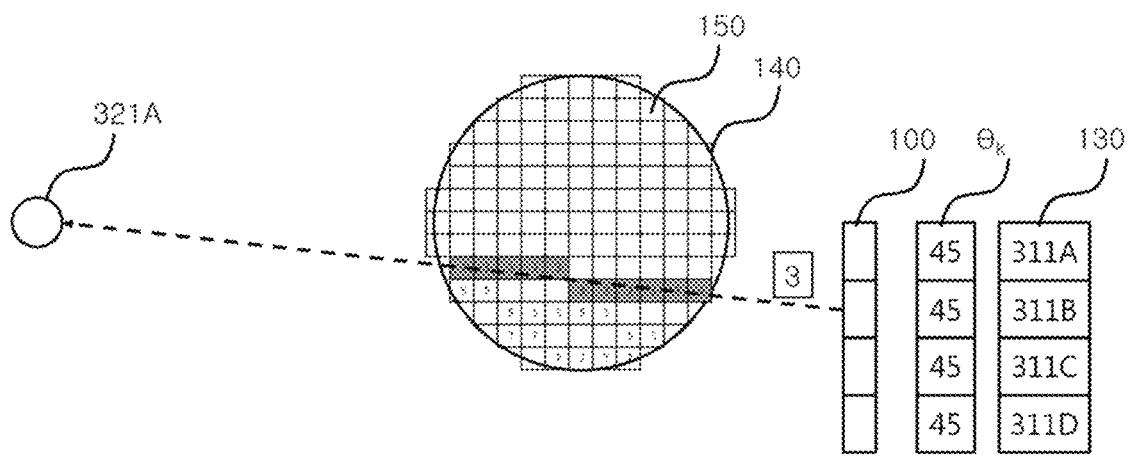
Figure 6E:
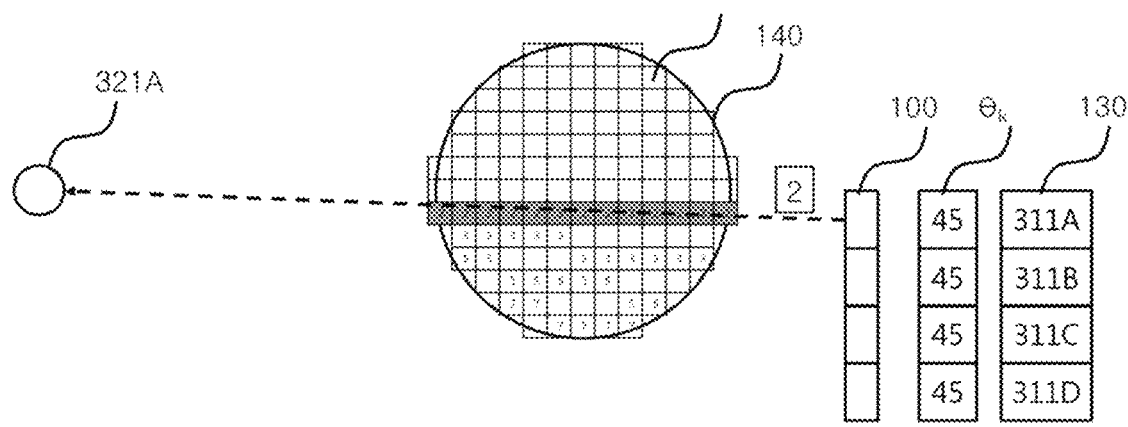

In FIGS. 6b to 6e, FIG. 6b shows a case of back-projecting one predetermined pixel of the divided projection image D2 in the synthetic projection image, that is, of the divided projection image D2 obtained corresponding to the imaging angle of 45 degrees and the fourth light receiving position 311D, FIG. 6c shows a case of back-projecting one predetermined pixel of the divided projection image C2 in the synthetic projection image, that is, of the divided projection image C2 obtained corresponding to the imaging angle of 45 degrees and the third light receiving position 311C, FIG. 6d shows a case of back-projecting one predetermined pixel of the divided projection image B2 in the synthetic projection image, that is, of the divided projection image B2 obtained corresponding to the imaging angle of 45 degrees and the second light receiving position 311B, and FIG. 6e shows a case of back-projecting one predetermined pixel of the divided projection image A2 in the synthetic projection image, that is, of the divided projection image A2 obtained corresponding to the imaging angle of 45 degrees and the first light receiving position 311A.

As shown in FIG. 6a, each of the divided projection image A2, B2, C2, and D2 in the synthetic projection image 100 has corresponding imaging angle information θ and receiving position information 130. When reconstruction is started, a reconstruction area 140 consisting of a plurality of voxels 150 corresponding to the entire FOV FA, FB, FC and FD is set on the reconstruction space. Next, by using the imaging angle information θ of each of the divided projection image A2, B2, C2, and D2 in the synthetic projection image 100, a virtual X-ray source 321A is set to the coordinates on the reconstruction space corresponding to the position of the X-ray source 321.

Next, as shown in FIG. 6b, a data value 7 of each pixel is inserted into each voxel 150 existing on a virtual X-ray connecting the spatial coordinate position of each pixel of the divided projection image D2 in the synthetic projection image 100 and the spatial coordinate position of the virtual X-ray source 321A.

Next, as shown in FIG. 6c, a data value 5 of each pixel is inserted into each voxel 150 existing on a virtual X-ray connecting the spatial coordinate position of each pixel of the divided projection image C2 in the synthetic projection image 100 and the spatial coordinate position of the virtual X-ray source 321A.

Next, as shown in FIG. 6d, a data value 3 of each pixel is inserted into each voxel 150 existing on a virtual X-ray connecting the spatial coordinate position of each pixel of the divided projection image B2 in the synthetic projection image 100 and the spatial coordinate position of the virtual X-ray source 321A.

Next, as shown in FIG. 6e, a data value 2 of each pixel is inserted into each voxel 150 existing on a virtual X-ray connecting the spatial coordinate position of each pixel of the divided projection image A2 in the synthetic projection image 100 and the spatial coordinate position of the virtual X-ray source 321A.

Although in the above description, only one pixel in each divided projection image has been described, it will be appreciated by those skilled in the art that in actual implementation, the above-described back projection should be performed for all the pixels in each divided projection image.

The processes shown in FIGS. 6b to 6e are performed for all the synthetic projection images 100 to generate a three-dimensional reconstructed image.

Figure 7:
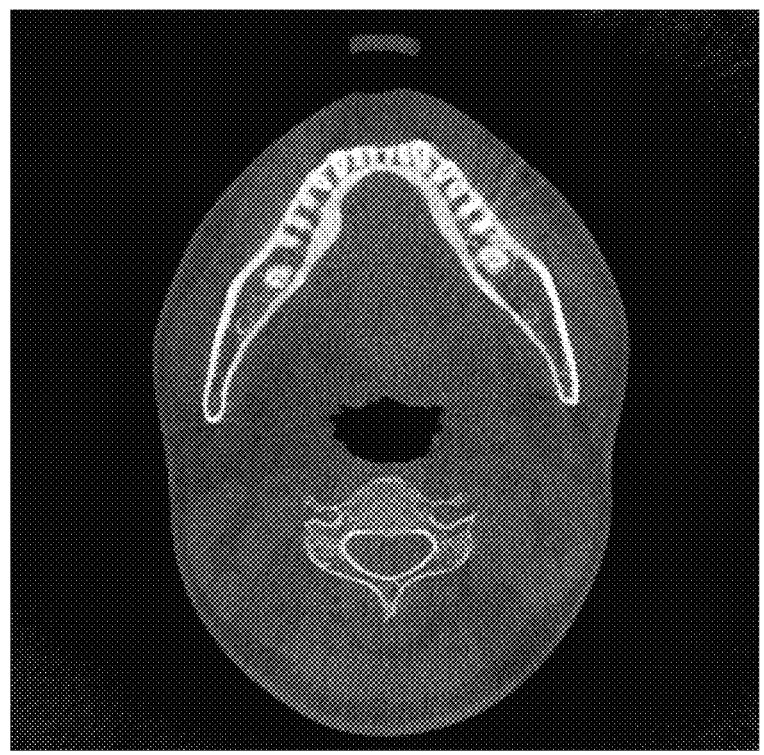
FIG. 7 is a sectional view showing a reconstructed image.

FIG. 7 is a sectional view showing a three-dimensional reconstructed image obtained by reconstructing synthetic projection images of FIG. 5.

Meanwhile, in the case of a reconstructed projection image through the above procedure, the divided projection images may not be obtained at the correct imaging angle, which may cause problems with the reconstructed image.

Therefore, in the present specification, a method for correcting an error in a reconstructed image caused by an error in imaging angle is proposed.

To this end, an X-ray image processing device for reconstructing a projection image obtained using a small X-ray detector according to the present invention stores a weight value for correcting a pre-measured error e for each imaging angle of the X-ray image processing device in the storage unit (not shown). The error e for each imaging angle is an error that occurs when the divided projection images are not acquired at a desired imaging angle. For example, the error is obtained by comparing the ideal reference projection images acquired for each imaging angle to a calibration object and the actual acquired projection images for each imaging angle to the calibration object. The nearest reference projection image is extracted by comparing the actual acquired projection image at a specific imaging angle with the reference projection images at the specific imaging angle and at a plurality of predetermined peripheral imaging angles adjacent thereto, the difference between the imaging angle of the nearest reference projection image and the specific imaging angle of the actually acquired projection image is obtained as an error θ for each imaging angle of the X-ray image processing device, and the weight value for correcting the error θ for each imaging angle is stored in the storage unit (not shown) inside the controller 70. Next, by using the stored weight value according to the error θ for each imaging angle, the projection image is corrected, thereby producing a more precise reconstructed image.

It is assumed that the error θ for each imaging angle is the same for every X-ray imaging.

Table 2 exemplarily shows the weight values for correcting the error θ for each imaging angle of the X-ray image processing device.

TABLE 2

| Light receiving position | Imaging angle | | | | | | | |
|---|---|---|---|---|---|---|---|---|
| | 0° | 45° | 90° | 135° | 180° | 225° | 270° | 315° |
| 311A | 1° | 0° | 0° | 0° | −1° | 0° | 2° | 1° |
| 311B | −1° | 1° | 0° | 0° | −1° | 1° | 0° | 0° |
| 311C | 0.5° | 0° | −1° | 1° | 1° | 0° | 0° | 0° |
| 311D | 0° | 0° | 0.1° | 2° | 0° | 0° | −1° | 0.1° |

The image reconstructor 60 of the X-ray image processing device reconstructs the synthetic projection images to obtain a three-dimensional reconstructed image, in consideration of information about the error for each imaging angle. This will be described with reference to FIGS. 8*a* to 8*e*.

Figure 8A:
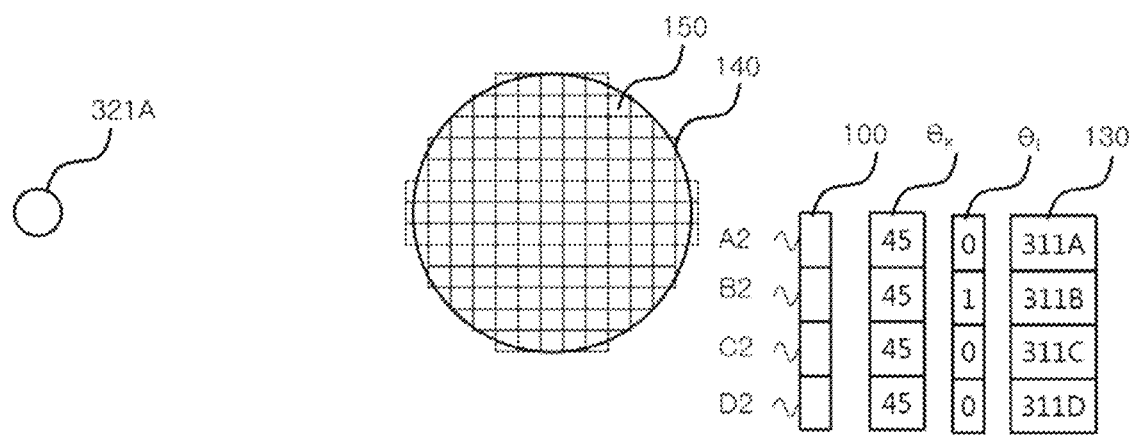
FIGS. 8*a* to 8*e* are views showing processes of reconstructing the synthetic projection image considering the information about error.
Figure 8B:
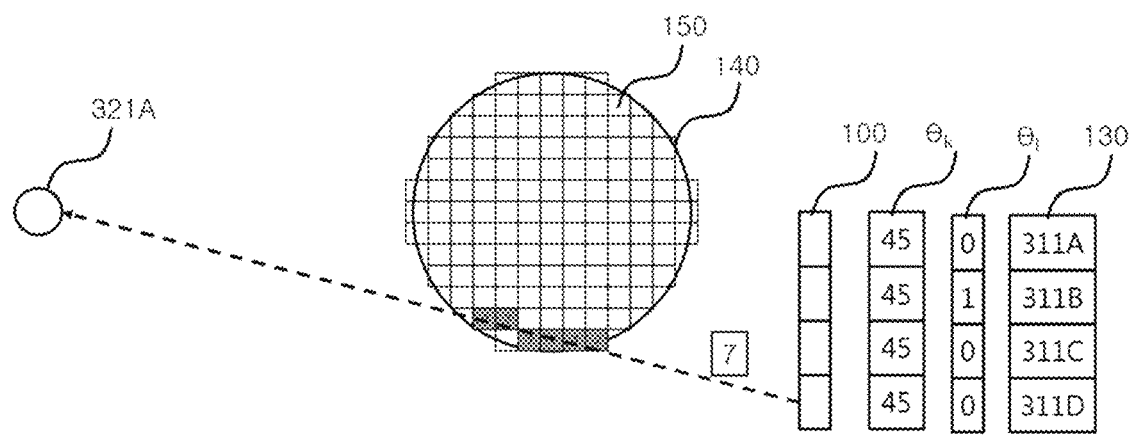
Figure 8C:
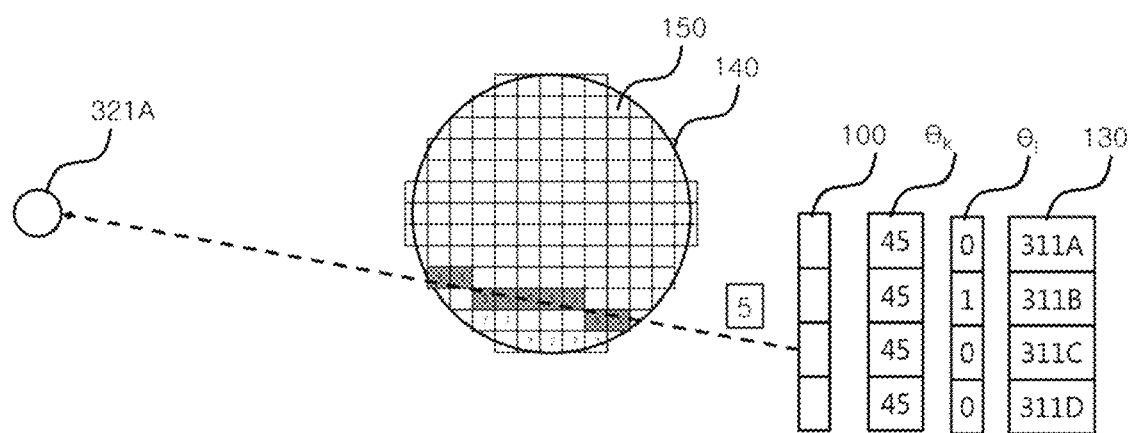
Figure 8D:
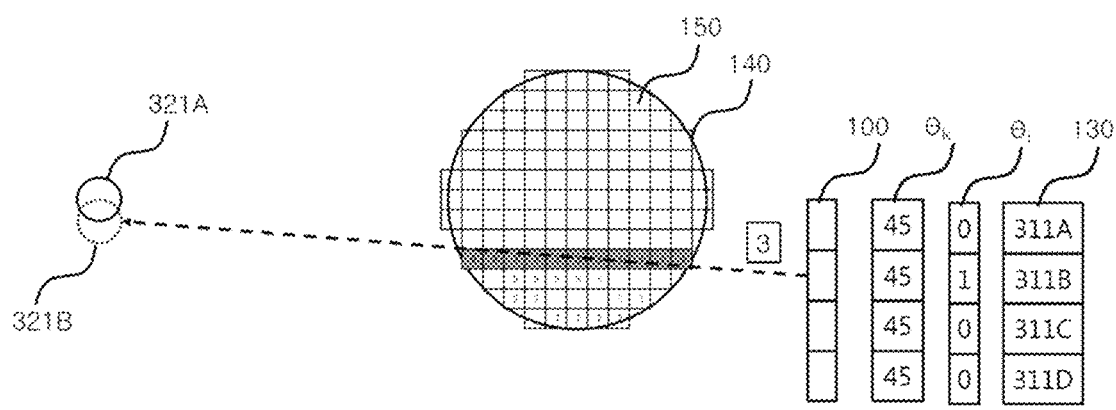
Figure 8E:
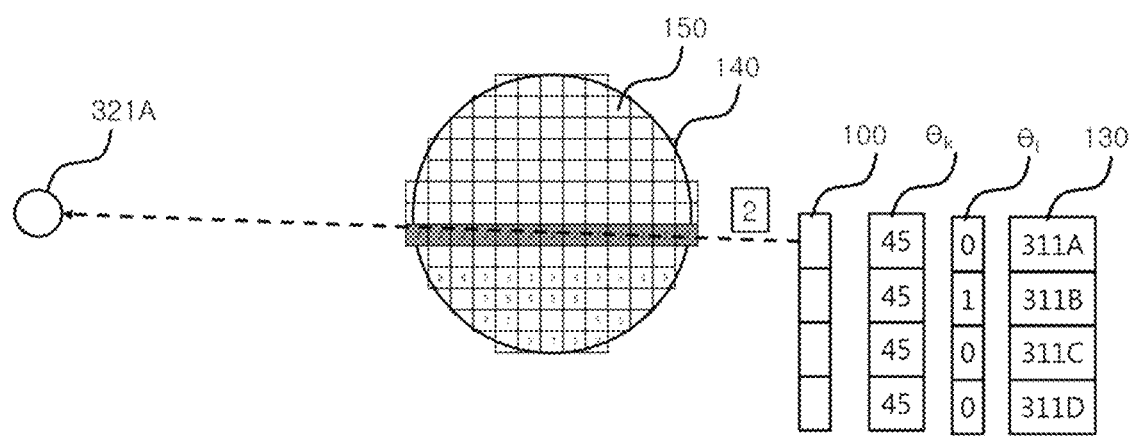

In FIGS. 8*b* to 8*e*, FIG. 8*b* shows a case of back-projecting one predetermined pixel of the divided projection image D2 in the synthetic projection image 100, that is, of the divided projection image D2 obtained corresponding to the imaging angle of 45 degrees and the fourth light receiving position 311D in consideration of a corresponding weight value (0 degree), FIG. 8*c* shows a case of back-projecting one predetermined pixel of the divided projection image C2 in the synthetic projection image 100, that is, of the divided projection image C2 obtained corresponding to the imaging angle of 45 degrees and the third light receiving position 311C in consideration of a corresponding weight value (0 degree), FIG. 8*d* shows a case of back-projecting one predetermined pixel of the divided projection image B2 in the synthetic projection image 100, that is, of the divided projection image B2 obtained corresponding to the imaging angle of 45 degrees and the second light receiving position 311B in consideration of a corresponding weight value (1 degree), and FIG. 8*e* shows a case of back-projecting one predetermined pixel of the divided projection image A2 in the synthetic projection image 100, that is, of the divided projection image A2 obtained corresponding to the imaging angle of 45 degrees and the first light receiving position 311A in consideration of a corresponding weight value (0 degree).

As shown in FIG. 8*a*, each of the divided projection image A2, B2, C2, and D2 in the synthetic projection image 100 has corresponding imaging angle information θ and receiving position information 130. When reconstruction is started, a reconstruction area 140 consisting of a plurality of voxels 150 corresponding to the entire FOV FA, FB, FC and FD is set on the reconstruction space. Next, by using the imaging angle information θ of each of the divided projection image A2, B2, C2, and D2 in the synthetic projection image 100, a virtual X-ray source 321A is set to the coordinates on the reconstruction space corresponding to the position of the X-ray source 321.

Next, as shown in FIG. 8*b*, in consideration of the weight value (0 degree) of the divided projection image D2 in the synthetic projection image 100, the spatial coordinate position of the virtual X-ray source 321A is corrected (in this case, since the weight value is 0 degree, the coordinate position of the virtual X-ray source 321A is not actually corrected), and the data value 7 of each pixel is inserted into each voxel 150 existing on a virtual X-ray connecting the spatial coordinate position of each pixel of the divided projection image D2 in the synthetic projection image 100 and the corrected spatial coordinate position of the virtual X-ray source 321A.

Next, as shown in FIG. 8*c*, in consideration of the weight value (0 degree) of the divided projection image C2 in the synthetic projection image 100, the spatial coordinate position of the virtual X-ray source 321A is corrected (in this case, since the weight value is 0 degree, the coordinate position of the virtual X-ray source 321A is not actually corrected), and the data value 5 of each pixel is inserted into each voxel 150 existing on a virtual X-ray connecting the spatial coordinate position of each pixel of the divided projection image C2 in the synthetic projection image 100 and the corrected spatial coordinate position of the virtual X-ray source 321A.

Next, as shown in FIG. 8*d*, in consideration of the weight value (1 degree) of the divided projection image B2 in the synthetic projection image 100, the spatial coordinate position of the virtual X-ray source 321A is corrected (in this case, the spatial coordinate position of the virtual X-ray source 321A is moved by 1 degree), and the data value 3 of each pixel is inserted into each voxel 150 existing on a virtual X-ray connecting the spatial coordinate position of each pixel of the divided projection image B2 in the synthetic projection image 100 and the corrected spatial coordinate position of the virtual X-ray source 321A.

Next, as shown in FIG. 8*e*, in consideration of the weight value (0 degree) of the divided projection image A2 in the synthetic projection image 100, the spatial coordinate position of the virtual X-ray source 321A is corrected (in this case, since the weight value is 0 degree, the coordinate position of the virtual X-ray source 321A is not actually corrected), and the data value 2 of each pixel is inserted into each voxel 150 existing on a virtual X-ray connecting the spatial coordinate position of each pixel of the divided projection image A2 in the synthetic projection image 100 and the corrected spatial coordinate position of the virtual X-ray source 321A.

The processes shown in FIGS. 8*b* to 8*e* are performed for all the synthetic projection images 100 to generate a three-dimensional reconstructed image.

Figure 9:
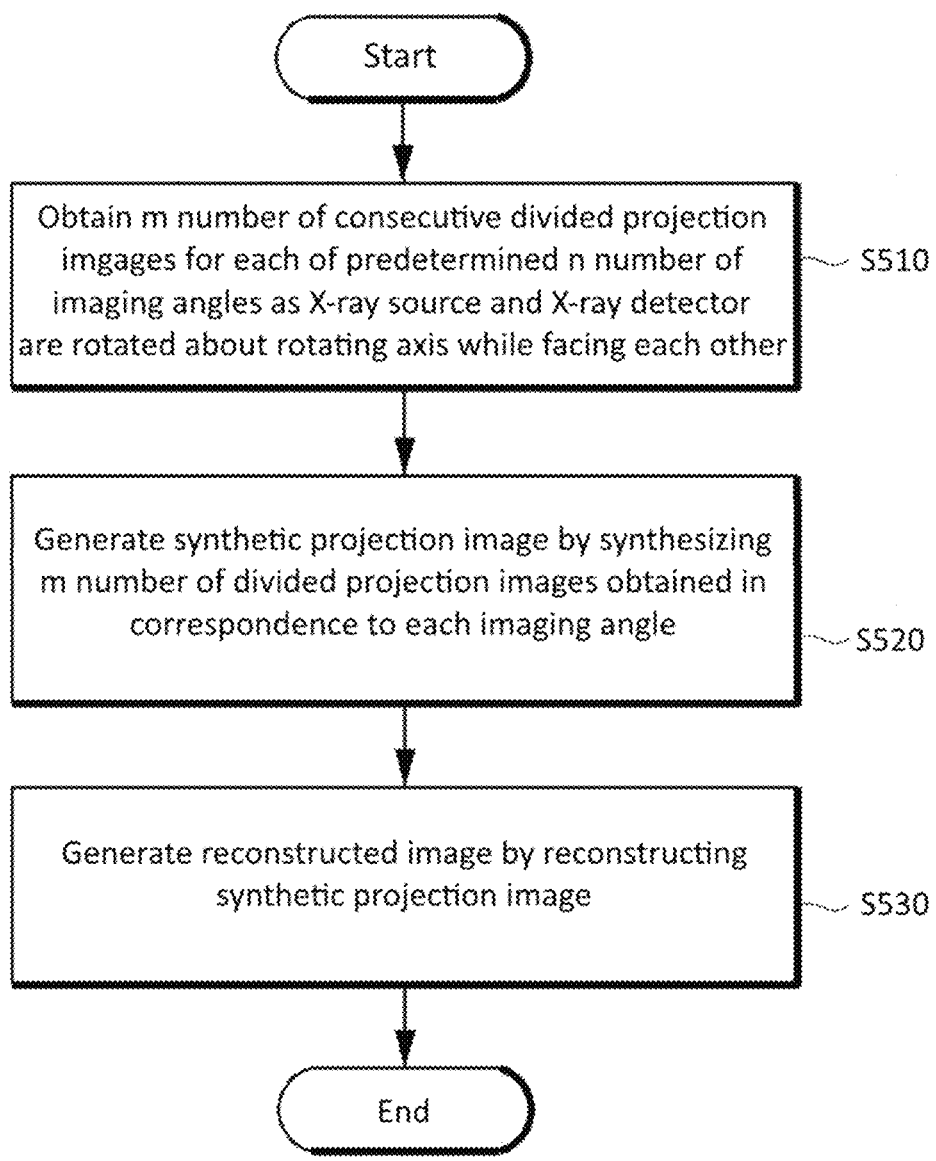
FIG. 9 is a view showing an X-ray image processing method according to the embodiment of the present invention.

FIG. 9 is a view showing an X-ray imaging method using a small X-ray detector according to the present invention.

The X-ray imaging method using a small X-ray detector according to the present invention obtains m (m is an integer of 2 or more) number of divided projection images at each of predetermined n (n is an integer of 1 or more) number of imaging angles about a rotating axis by moving an X-ray detector in a width direction across the rotating axis while rotating an X-ray source and the X-ray detector with the same facing each other about the rotating axis interposed therebetween (S510).

Here, the X-ray source and the X-ray detector are rotatable m*360 degrees, thereby obtaining m (m is an integer of 2 or more) number of divided projection images for each imaging angle Next, a synthetic projection image at each of the imaging angles is generated using the m number of divided projection images at each of the imaging angles (S520).

Next, a reconstructed image is generated by reconstructing the synthetic projection image (S530).

Here, before reconstructing the synthetic projection image, the m number of divided projection images at each of the imaging angles may be corrected with a same imaging angle for the rotating axis. To achieve this, multiple reference projection images at each imaging angle may be obtained from the predetermined n number of imaging angles and multiple imaging angles adjacent thereto, a projection image closest to the m number of projection images at each of the imaging angles may be obtained, and imaging angles of the m number of projection images at each of the imaging angles may be corrected along an imaging angle of the closest projection image at each of the imaging angles, whereby the m number of divided projection images at each of the imaging angles are corrected with the same imaging angle for the rotating axis. Such correction of the imaging angle for each imaging angle has been described in detail above and is therefore omitted.

Meanwhile, for the convenience, in the above description, the widthwise movement of the X-ray detector 311 has been described as being stepwise with respect to the rotation of the rotating arm 30 based on the rotating axis 25C, but the widthwise movement of the X-ray detector 311 may be performed simultaneously with the rotation of the rotating arm 30 based on the rotating axis 25C. Further, for the convenience, the X-ray detector 311 has been described as moving from the inside to the outside of the FOV, but the reverse thereof is possible. Here, the rotating speed of the rotating arm 30 and the moving speed of the X-ray detector 311 in the width direction can constantly work together and can be proportional to each other.

On the other hand, an X-ray image processing method for reconstructing a projection image obtained using the above described small X-ray detector may be implemented in the form of a program command that can be executed through various computer means and recorded in a computer-readable medium. The computer-readable medium may include program instructions, data files, data structures, etc., alone or a combination thereof. The program instructions recorded on the medium may be those specially designed and constructed for the present invention or may be available to those skilled in the art of computer software. Examples of computer-readable media may include magnetic media such as hard disks, floppy disks and magnetic tape, optical media such as CD-ROMs and DVDs, magneto-optical media such as floptical disks, and hardware devices that are specially configured to store and execute program instructions such as ROM, RAM, flash memory, and the like. The medium may be a transmission medium such as optical or metal lines, waveguides, etc., including a carrier wave for transmitting a signal specifying a program command, a data structure. Examples of program instructions include machine language code such as those produced by a compiler, as well as high-level language code that can be executed by a computer using a decoder or the like. The hardware device may be configured to operate as one or more software modules to perform operations of the present invention, and vice versa.

Although a preferred embodiment of the present invention has been described for illustrative purposes, those skilled in the art will appreciate that various modifications, additions and substitutions are possible, without departing from the scope and spirit of the invention.

For example, although it is shown that the present invention obtains a divided projection image using a circular trajectory in FIGS. 2a to 2d, the present invention can obtain divided projection images using not only a circular trajectory but also a spiral trajectory.

Therefore, the scope of the present invention should be interpreted by the accompanying claims, and it is to be understood that all technical ideas within the claims fall within the purview of the present invention.

The invention claimed is:

1. An X-ray image processing method comprising:
   (a) obtaining a plurality of multi directional divided projection images of a subject by rotating an X-ray source and an X-ray detector about a rotating axis with the subject interposed therebetween and moving the X-ray detector in a width direction across the rotating axis;
   (b) classifying the multi directional divided projection images according to predetermined imaging angles about a rotating axis;
   (c) generating a synthetic projection image at each of the imaging angles using the divided projection images classified into same imaging angle; and
   (d) generating a reconstructed image by reconstructing the synthetic projection image.

2. The method of claim 1, wherein in the (a) step, the X-ray source and the X-ray detector are rotated m*360 degrees.

3. The method of claim 1, after the (a) step and before the (d) step, further comprising
   correcting the multi directional divided projection images at each of the imaging angles with a same imaging angle for the rotating axis.

4. The method of claim 3, wherein after the (a) step and before the (d) step, multiple reference projection images at each imaging angle are obtained from the predetermined imaging angles and multiple imaging angles adjacent thereto;
   a projection image closest to the multi directional divided projection images at each of the imaging angles is obtained from the multiple reference projection images; and
   imaging angles of the multi directional divided projection images at each of the imaging angles are corrected along an imaging angle of the closest projection image at each of the imaging angles,
   whereby the multi directional divided projection images at each of the imaging angles are corrected with the same imaging angle for the rotating axis.

5. An X-ray image processing device comprising:
   a divided projection image obtaining unit configured to obtain a plurality of multi directional divided projection images of a subject by rotating an X-ray source and an X-ray detector about a rotating axis with the subject interposed therebetween and moving the X-ray detector in a width direction across the rotating axis;
   a projection image classifying unit configured to classifying the multi directional divided projection images according to the imaging angles;
   a projection image synthesizing unit configured to generate a synthetic projection image at each of the imaging angles using the m number of divided projection images at classified into samel imaging angle and
   an image reconstructor configured to generate a reconstructed three-dimensional image by reconstructing the synthetic projection image.

6. The device of claim 5, wherein the divided projection image obtaining unit rotates the X-ray source and the X-ray detector m*360 degrees.

7. The device of claim 5, wherein the image reconstructor corrects the multi directional divided projection images at each of the imaging angles with a same imaging angle for the rotating axis to generate the reconstructed three-dimensional image.

8. The device of claim 7, wherein the image reconstructor obtains multiple reference projection images at each imaging angle from the predetermined imaging angles and multiple imaging angles adjacent thereto, obtains a projection image closest to the multi directional divided projection images at each of the imaging angles, from the multi reference projection image, and corrects imaging angles of the multi directional divided projection images at each of the imaging angles along an imaging angle of the closest projection image at each of the imaging angles, thereby correcting the multi directional divided projection images at each of the imaging angles with the same imaging angle for the rotating axis.

\* \* \* \* \*